US012558215B2

(12) United States Patent
Heckler, II et al.

(10) Patent No.: US 12,558,215 B2
(45) Date of Patent: Feb. 24, 2026

(54) SOFT TIP PLUNGER

(71) Applicant: Alcon Inc., Fribourg (CH)

(72) Inventors: Paul Heckler, II, Irvine, CA (US);
Kathryn Jensen, Sugar Land, TX (US);
Matthew Douglas McCawley, San
Clemente, CA (US); Chris Renner,
Irvine, CA (US); Sudarshan B. Singh,
Euless, TX (US); Todd Taber, Keller,
TX (US)

(73) Assignee: Alcon Inc., Fribourg (CH)

( * ) Notice: Subject to any disclaimer, the term of this
patent is extended or adjusted under 35
U.S.C. 154(b) by 635 days.

(21) Appl. No.: 17/033,448

(22) Filed: Sep. 25, 2020

(65) Prior Publication Data

US 2021/0093447 A1      Apr. 1, 2021

Related U.S. Application Data

(60) Provisional application No. 62/908,307, filed on Sep.
30, 2019.

(51) Int. Cl.
*A61F 2/16* (2006.01)
*C08L 69/00* (2006.01)

(52) U.S. Cl.
CPC ............ *A61F 2/1678* (2013.01); *C08L 69/00*
(2013.01); *A61F 2002/1681* (2013.01)

(58) Field of Classification Search
CPC ............ A61F 2/1678; A61F 2002/1681; A61F
2/1662; A61F 2/167; A61F 2/966
See application file for complete search history.

(56) References Cited

U.S. PATENT DOCUMENTS

| | | | | |
|---|---|---|---|---|
| 5,174,292 A | * | 12/1992 | Kursar | A61B 3/16 |
| | | | | 600/405 |
| 5,425,734 A | * | 6/1995 | Blake | A61F 2/1664 |
| | | | | 606/107 |
| 5,494,484 A | * | 2/1996 | Feingold | A61F 2/167 |
| | | | | 606/107 |
| 5,514,125 A | * | 5/1996 | Lasser | A61F 9/00781 |
| | | | | 606/4 |
| 5,735,858 A | * | 4/1998 | Makker | A61F 2/1678 |
| | | | | 606/107 |
| 5,772,666 A | * | 6/1998 | Feingold | A61F 2/1678 |
| | | | | 606/107 |

(Continued)

FOREIGN PATENT DOCUMENTS

| | | | | | |
|---|---|---|---|---|---|
| CN | 1845712 B | * | 4/2010 | ............. | A61F 2/167 |
| EP | 2062552 A1 | | 5/2009 | | |

(Continued)

OTHER PUBLICATIONS

WO2020186365A1 Espacenet translation (Year: 2020).*

*Primary Examiner* — Darwin P Erezo
*Assistant Examiner* — Zehra Jaffri
(74) *Attorney, Agent, or Firm* — PATTERSON +
SHERIDAN, LLP

(57) ABSTRACT

Systems, methods, and devices for inserting an intraocular
lens (IOL) into an eye, may be provided. An apparatus
includes a plunger and a plunger tip. The plunger tip
includes a dimple positioned at a distal end of the plunger
tip. The plunger tip further includes a pocket in fluid
communication with the dimple.

11 Claims, 17 Drawing Sheets

(56)        References Cited

U.S. PATENT DOCUMENTS

| | | | | | |
|---|---|---|---|---|---|
| 5,800,442 | A | * | 9/1998 | Wolf | A61F 2/167 |
| | | | | | 606/107 |
| 6,162,229 | A | * | 12/2000 | Feingold | A61F 2/1664 |
| | | | | | 606/107 |
| 7,335,209 | B2 | * | 2/2008 | Meyer | A61F 2/1664 |
| | | | | | 606/107 |
| 9,662,200 | B2 | * | 5/2017 | Muchhala | B05D 7/02 |
| | | | | | 606/107 |
| 2003/0195522 | A1 | * | 10/2003 | McNicholas | A61F 2/1678 |
| | | | | | 606/107 |
| 2003/0216745 | A1 | * | 11/2003 | Brady | A61F 2/1678 |
| | | | | | 606/103 |
| 2004/0111094 | A1 | * | 6/2004 | Meyer | A61F 2/1664 |
| | | | | | 606/107 |
| 2005/0143751 | A1 | * | 6/2005 | Makker | G02B 1/043 |
| | | | | | 606/107 |
| 2006/0173539 | A1 | * | 8/2006 | Shiuey | A61F 2/145 |
| | | | | | 623/5.11 |
| 2008/0027461 | A1 | * | 1/2008 | Vaquero | A61F 2/1664 |
| | | | | | 606/107 |
| 2010/0121340 | A1 | * | 5/2010 | Downer | A61F 2/167 |
| | | | | | 606/107 |
| 2012/0022549 | A1 | * | 1/2012 | Someya | A61F 2/167 |
| | | | | | 606/107 |
| 2014/0200588 | A1 | * | 7/2014 | Anderson | A61F 2/1672 |
| | | | | | 606/107 |
| 2014/0316425 | A1 | * | 10/2014 | Ossipov | B05D 7/02 |
| | | | | | 606/107 |
| 2016/0305825 | A1 | * | 10/2016 | Chokri | A61F 2/167 |
| | | | | | 606/107 |
| 2017/0202662 | A1 | * | 7/2017 | Someya | A61F 2/1678 |
| 2017/0367817 | A1 | | 12/2017 | Belisle | |
| 2018/0200046 | A1 | | 7/2018 | Brown | |
| 2018/0200047 | A1 | | 7/2018 | Wu | |
| 2019/0175335 | A1 | * | 6/2019 | Glick | A61F 2/1691 |

FOREIGN PATENT DOCUMENTS

| | | | | | |
|---|---|---|---|---|---|
| EP | | 2926770 | A1 | 10/2015 | |
| JP | | 2009-028223 | A | 2/2009 | |
| JP | | 2010273985 | A | 12/2010 | |
| WO | | 2007005692 | A1 | 1/2007 | |
| WO | WO-2015193046 | A1 | * | 12/2015 | A61F 2/167 |
| WO | WO-2020186365 | A1 | * | 9/2020 | A61F 2/1678 |

* cited by examiner

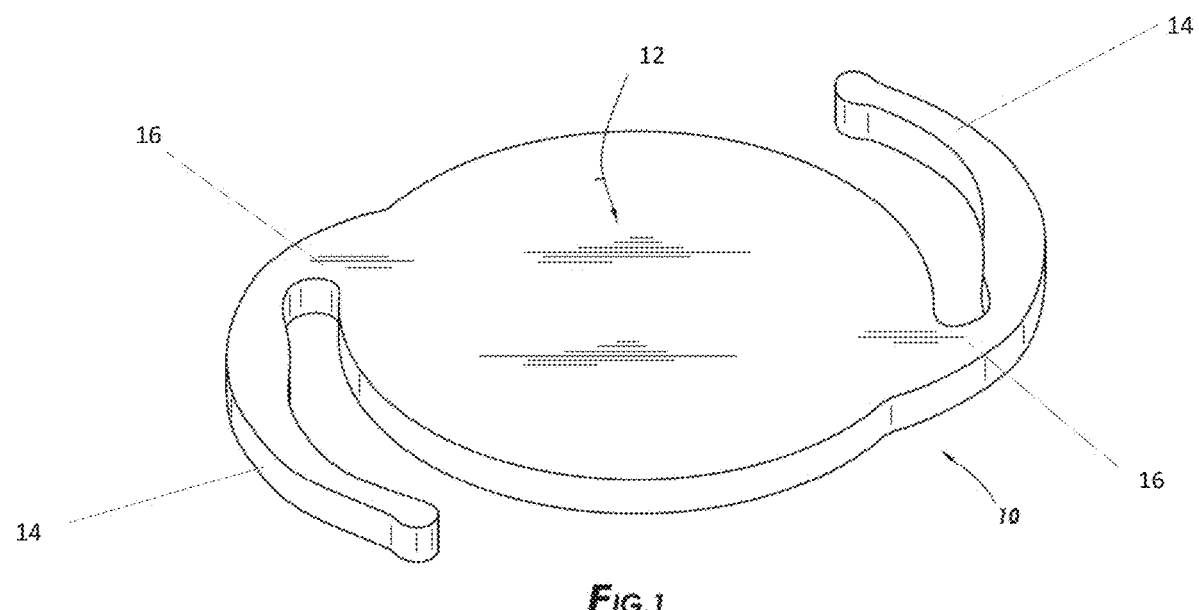
*F*IG.1

70
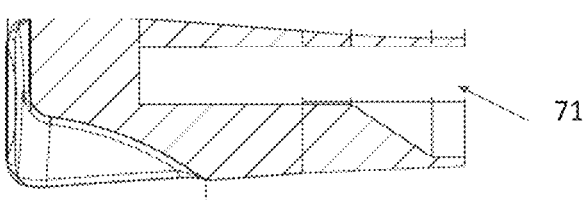
71
FIG. 7C 88    86

91

SOFT TIP PLUNGER

TECHNICAL FIELD

The present disclosure generally relates to eye surgery and, more particularly, some embodiments may generally relate to systems, methods, and devices for inserting an intraocular lens (IOL) into an eye with a soft tip plunger.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded lens with an intraocular lens (IOL). An insertion tool can be used for delivery of the IOL into the eye. By way of example, the insertion tool may include a plunger for forcing the IOL out of the nozzle of the insertion tool. In some instances, the IOL may be pre-loaded in the insertion tool. In other instances, a separate bay may be loaded into the insertion tool. The plunger may engage the IOL to advance the IOL from the bay, through the nozzle, and into the eye. The bay (or insertion tool) may include a folding chamber configured to cause the IOL to fold, for example, when the IOL advances through the folding chamber. In some instances, a separate action may cause folding of the IOL.

Delivery of the IOL from the insertion tool can be a multi-step process. For example, the delivery may include two stages, which may be referred to as an advancing stage and a delivery stage. In the advancing stage, the IOL can be advanced from a storage position in the bay to a dwell position. The IOL may be pre-folded or may be folded when advanced from the storage position to the dwell position. At the dwell position, advancement of the IOL may be halted, the nozzle positioned in the eye, the IOL may then be further advanced from the dwell position, in the delivery stage, which may include advancing the IOL through the nozzle and into the eye.

SUMMARY

In an exemplary embodiment, the present disclosure provides an apparatus for delivery of an IOL into an eye. The apparatus includes a plunger and a plunger tip. The plunger tip includes a dimple positioned at a distal end of the plunger tip. The plunger tip further includes a pocket that is in fluid communication with the dimple.

In another exemplary embodiment, the present disclosure provides an apparatus, for delivery of an IOL into an eye, that includes a nozzle and a cartridge. The cartridge is coupled to the nozzle, and the plunger is aligned with an aperture of the cartridge. A plunger tip comprises a dimple positioned at a distal end of the plunger tip. A pocket is in fluid communication with the dimple.

In another exemplary embodiment, the present disclosure provides a method for delivery of an IOL into an eye. The method includes inserting a nozzle of an insertion tool into the eye through an incision. The insertion tool further comprises a plunger and a plunger tip. The plunger tip includes a dimple positioned at a distal end of the plunger tip. The plunger tip also includes a pocket that is in fluid communication with the dimple.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

FIG. 1 illustrates an IOL in accordance with some embodiments of the present disclosure;

FIG. 7C illustrates a cross-section of the soft tip of FIG. 7A in accordance with some embodiments of the present disclosure;

DETAILED DESCRIPTION

Figures 2A, 2B:
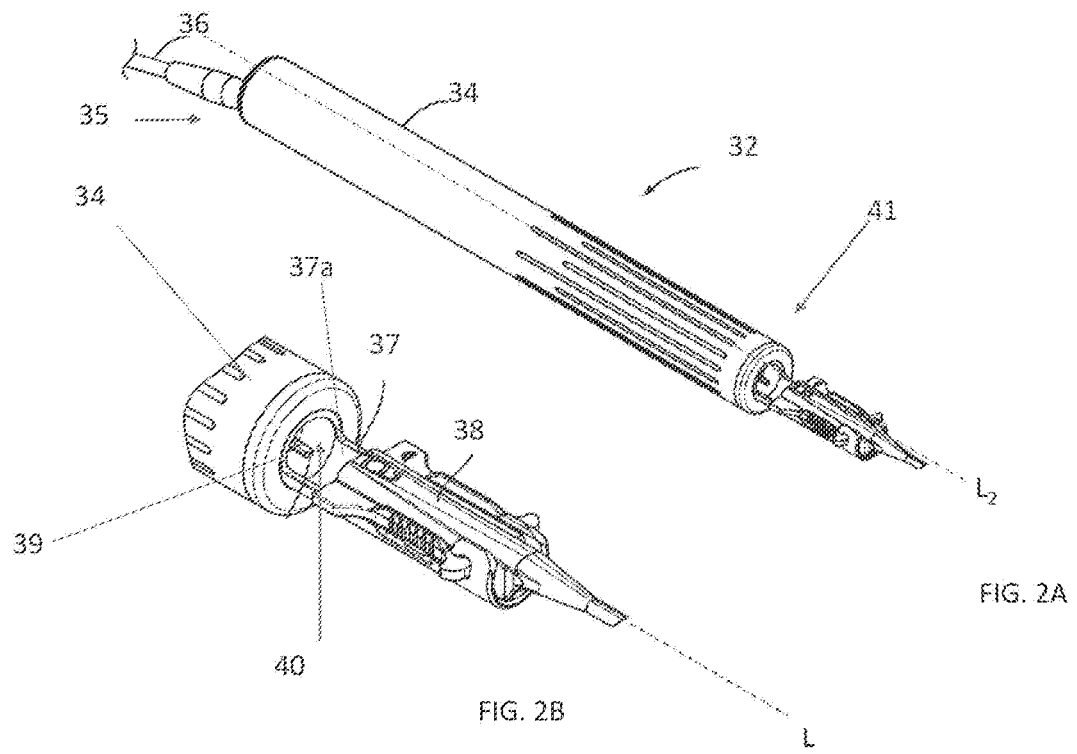
FIG. 2A illustrates a perspective view of an insertion tool, in accordance with some embodiments of the present disclosure.
FIG. 2B illustrates a close-up view of the insertion tool of FIG. 2A in accordance with some embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Some embodiments of the present disclosure provide an improvement over existing soft tip plungers common in manually loaded IOL delivery systems. Previous soft tip plungers were of a solid cylinder "plug"-type. These solid cylinder plunger tips may damage the IOL during delivery into an eye. For example, a solid cylinder plunger tip may crush a gusset and/or a trailing haptic during compression and delivery of the IOL. Some embodiments described herein provide a more advanced geometry to prevent damage to the IOL during delivery. Specifically, some embodiments described herein include a soft tip of a plunger that includes surface topography. The surface topography may include contours such as a dimple and/or a pocket to provide relief for the gusset and/or the trailing haptic attached thereto, as the IOL is compressed during delivery. This relief may prevent damage to the IOL.

Particular embodiments of the present disclosure are directed to a plunger that may be packaged in a preloaded system utilized for IOL delivery through an incision that may be less than 2.0 millimeters ("mm") in diameter. The plunger is configured to engage and advance the IOL from a cartridge and deliver the IOL without damaging the IOL. Particular embodiments of the present disclosure include a rigid geometric substrate used to improve IOL engagement and delivery. This substrate may be surrounded by a soft material or soft tip that provides sufficient cushion to prevent IOL damage during delivery.

FIG. 1 illustrates an IOL 10 in accordance with some embodiments of the present disclosure. The IOL 10 may be any suitable intraocular lens. The IOL 10 may include a lens portion 12 and haptic extensions 14. The haptic extensions 14 may be side struts (or other suitable extensions) extending from the lens portions 12 that may stabilize the IOL 10 when it may be disposed within the patient's eye. Gussets 16 may be shoulders or portions of the lens portion 12 from which the haptic extensions 14 extend from. It should be understood that the IOL 10 shown in FIG. 1 is merely exemplary and that techniques disclosed herein may be used with any suitable IOL. For example, a modular IOL (not shown) that includes a lens portion disposable in a base with haptic extensions can also be used.

FIGS. 2A and 2B illustrate an insertion tool 32 for implanting the IOL 10 into an eye, in accordance with particular embodiments of the present disclosure. It should be noted that the insertion tool 32 is a non-limiting example, and that other types of insertion tools (e.g., tools that are manual or not powered with electricity) may be utilized with a soft tip plunger (e.g., shown on FIGS. 5A and 5B). As shown on FIG. 2A, the insertion tool 32 may include a housing 34. The housing 34 may generally be of a tubular shape and may include a proximal end or first end 35 opposite to a distal end or a second end 41. A cable 36 that carries power and/or control signals from a separate user console (not shown), may extend from first end 35. In certain embodiments, the insertion tool 32 may include a battery.

FIG. 2B is a close-up view of the second end 41 in accordance with particular embodiments of the present disclosure. As shown, the insertion tool 32 may also include a cartridge mount 37 that holds a removably mounted insertion cartridge 38. The insertion cartridge 38 may be a disposable polymeric component adapted to accommodate an unfolded IOL 10 and to fold and displace the IOL 10 as the plunger is translated forward from the housing 34 and through the insertion cartridge 38, in accordance with exemplary embodiments.

The cartridge mount 37 may be a rigid member that extends from the second end 41. In some embodiments, the cartridge mount 37 may comprise a metallic cutout or curved inner surface 37a to accommodate the insertion cartridge 38. In particular embodiments, an end 39 of the cartridge mount 37 may be press-fitted into a passage 40 that extends through the housing 34 and along the longitudinal axis L of the housing 34, as shown.

Figure 3:
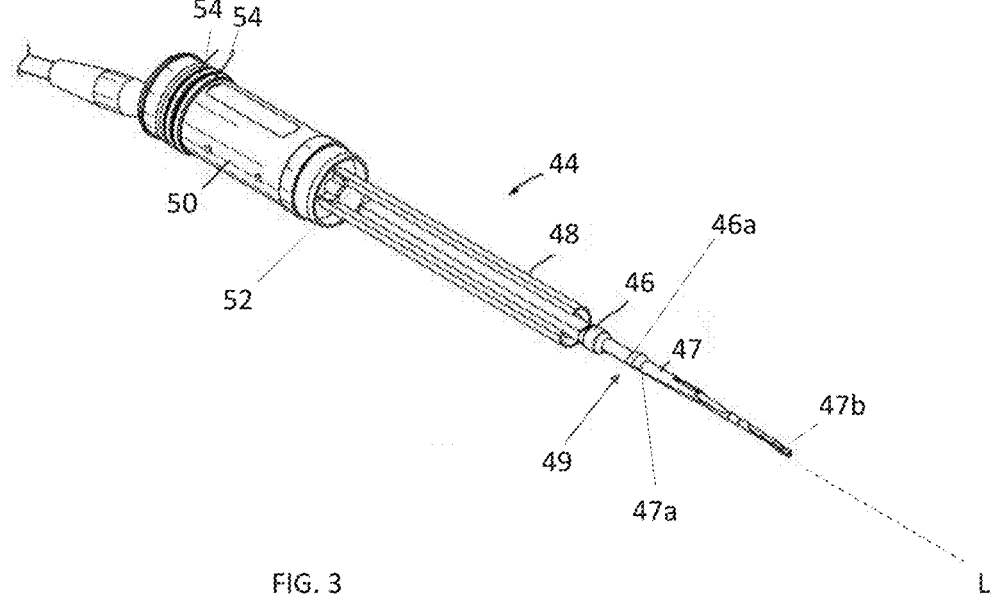
FIG. 3 illustrates a partially cut-away view of the insertion tool in accordance with some embodiments of the present disclosure.

FIG. 3 illustrates a partially cut-away view of an exemplary embodiment of the insertion tool 32, showing an actuating assembly 44 disposed within the housing 34 (e.g., shown on FIG. 2A). The actuating assembly 44 may linearly translate a plunger 47 along the longitudinal axis L of the housing 34.

The actuating assembly 44 includes a shaft 46 configured for longitudinal translation inside a threaded (internally threaded) tubular coupler 48. The shaft 46 may be coupled to a drive system 50 and the plunger 47, as shown. The plunger 47 may be removably coupled to the shaft 46 via a snap-fit mechanism 49. In some embodiments, the snap-fit mechanism 49 includes portion 46a of the shaft 46 that interlocks with portion 47a of the plunger 47. The portion 47a may be opposite from a distal end 47b of the plunger 47, as shown. The drive system 50 may include components such as an electric motor and gear set configured to rotate the tubular coupler 48 to force linear translation of the shaft 46 and the plunger 47 within the tubular coupler 48. As shown, the tubular coupler 48 may engage a threaded (exterior threads) coupler 52 at the rear end of the shaft 46, forcing linear translation of the shaft 46, in response to activation of the drive system 50. O-rings 54, which may be formed from an elastomer, can provide a seal between the housing 34 and the actuating assembly 44, preventing moisture and/or other contaminants from reaching the interior of the housing 34.

Figure 4:
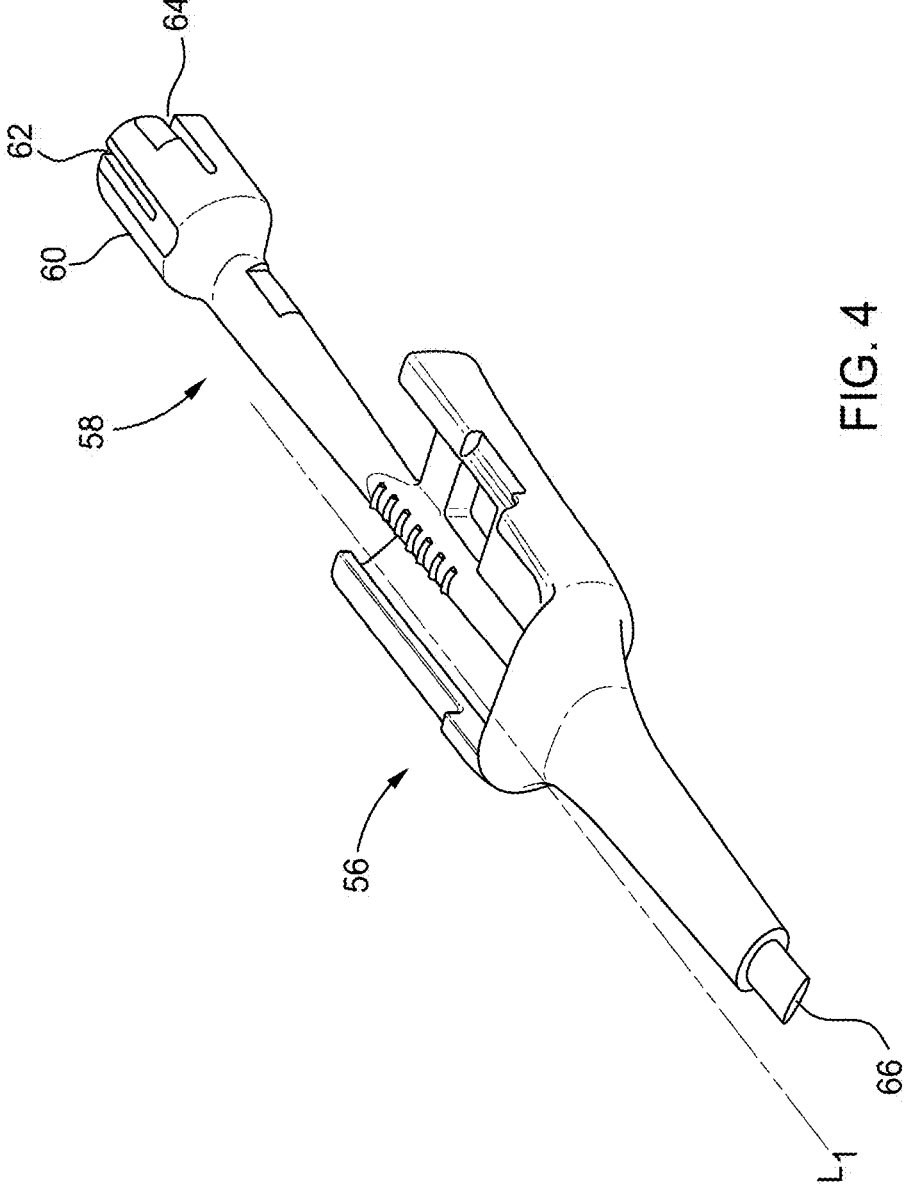
FIG. 4 illustrates a partially cut-away view of an insertion cartridge in accordance with some embodiments of the present disclosure.

FIG. 4 illustrates a partially cut-away view of an insertion cartridge 56 in accordance with particular embodiments of the present disclosure. The insertion cartridge 56 may be similar to the insertion cartridge 38 (e.g., shown on FIG. 2B). FIG. 4 also illustrates a plunger 58 that may be similar to the plunger 47 (e.g., shown on FIG. 3) in accordance with particular embodiments of the present disclosure. The plunger 58 may include a portion 60 that is similar to the portion 47a (e.g., shown on FIG. 3). It should be noted that the plunger 58 is a non-limiting example, and that other types of plungers may be utilized. As shown, the portion 60 may include features such as a groove 62 and a recess 64. The portion 46a of the snap-fit mechanism 49 (e.g., shown on FIG. 3) includes features that complement or correspond to the groove 62 and the recess 64 to secure or "snap" together the portions 46a and 60. A nozzle 66 may be positioned at a distal end of the insertion cartridge 56, as shown.

Figure 5A:
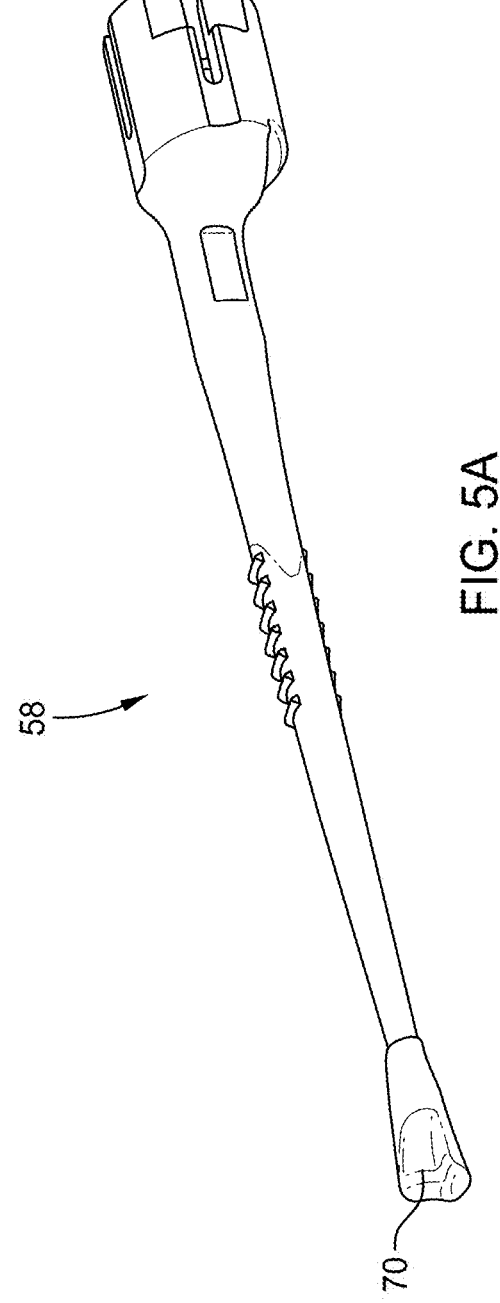
FIG. 5A illustrates a soft tip plunger in accordance with some embodiments of the present disclosure.

FIG. 5A illustrates a perspective view of the plunger 58 with a soft tip 70 in accordance with particular embodiments of the present disclosure. The soft tip 70 may be disposed at a distal end 72 (e.g., shown on FIG. 6) of the plunger 58. In some embodiments, the soft tip 70 may be overmolded onto the distal end 72. In some embodiments, the soft tip 70 may be adapted to provide a cushioning or non-abrasive engagement with the IOL 10, for example, as compared to the distal end 72. The soft tip 70 may include smooth surface(s) and may be elastomeric. In particular embodiments, the soft tip 70 may be formed from silicone.

The soft tip 70 may be made from any suitable medically compliant soft material. Without limitation, the soft tip 70 may be made of styrenic block copolymers, polyolefin blends ("TPOs"), elastomeric alloys, thermoplastic polyurethanes ("TPUs"), thermoplastic copolyesters, thermoplastic polyamides, or combinations thereof. The plunger 58 may be made of polystyrene, acrylonitrile butadiene styrene, polycarbonate, polyamide, polyimide, polyetherimide, polyarylamide, polyetheretherketone, polybutylene terephthalate, polypropylene, polysulphone, liquid crystal polymer, or combinations thereof. In some embodiments, the material forming the soft tip 70 may have a Shore A durometer value of about 30 to about 95. As used herein, durometer values are Shore hardness values as measured using ASTM D2250 type A and type D scales.

Figure 5B:
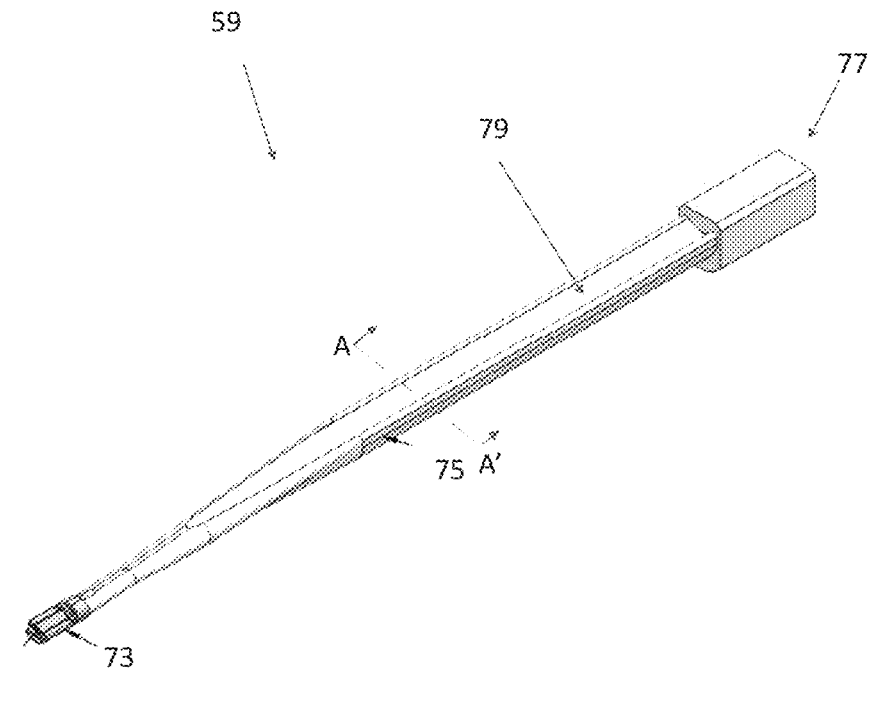
FIG. 5B illustrates an alternate plunger in accordance with some embodiments of the present disclosure.

FIG. 5B illustrates a perspective view of a plunger 59 with a distal end 73 in accordance with particular embodiments of the present disclosure. The plunger 59 may include an elongated substrate 75 extending from a connector 77 utilized to connect the plunger 50 to an insertion tool, such as the insertion tool 32 for example. The plunger 59 may include a channel 79 to facilitate actuation of the plunger 59 from, for example, the housing 34 of the insertion tool 32. In some embodiments, the plunger 59 may include features similar to the plunger 58. For example, the plunger 59 may be made of a polycarbonate. Additionally, the distal end 73 may be similar to the distal end 47b in some aspects. A soft tip 81 that may be overmolded onto the distal end 73 is described in further detail below (see FIGS. 7D-7F for example).

Figure 5C:
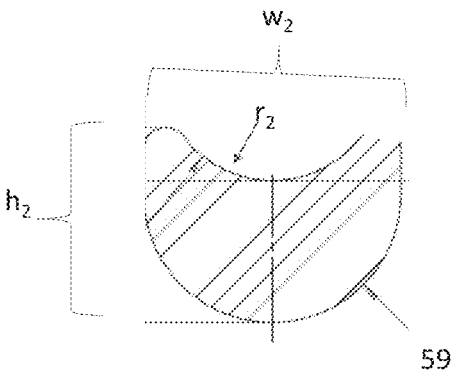
FIG. 5C illustrates a cross-section of the plunger of 5B in accordance with some embodiments of the present disclosure.

FIG. 5C illustrates a cross-section of the plunger 59 in accordance with particular embodiments of the present disclosure. The cross-section is taken along the dashed line extending from A to A', as shown on FIG. 5B. As shown on FIG. 5C, the plunger 59 may include a width ($w_2$) and a height ($h_2$), as shown. The channel 79 may be curved and include a radius of curvature $r_2$ ranging from 1 mm to 2 mm (e.g., 1.25 mm to 1.35 mm)

Figure 6:
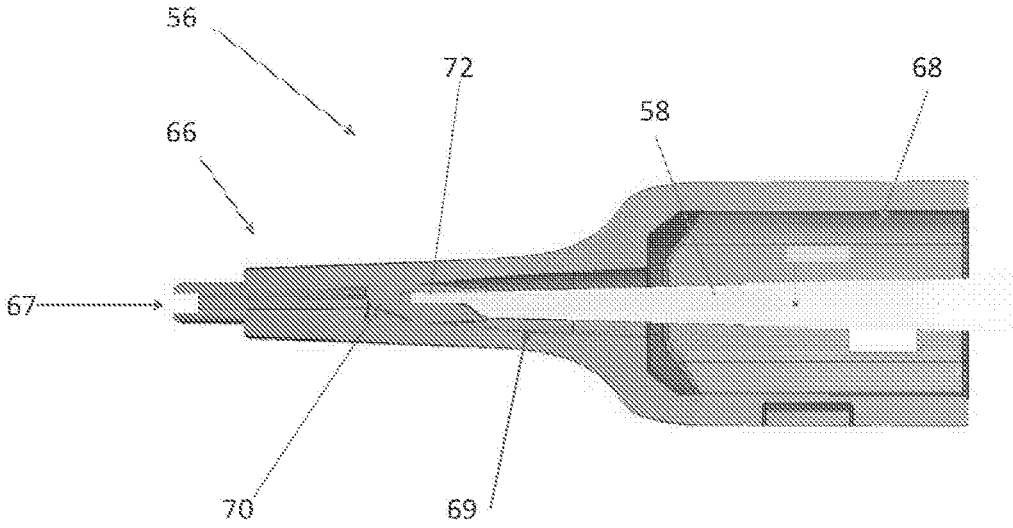
FIG. 6 illustrates a cross-section of an insertion cartridge in accordance with some embodiments of the present disclosure.

FIG. 6 illustrates a cross-section of the insertion cartridge 56 taken along the dashed line, $L_1$, as shown on FIG. 4, in accordance with particular embodiments of the present disclosure. As shown on FIG. 6, the plunger 58 may be movably (e.g., axially movable) disposed within the insertion cartridge 56. The nozzle 66 may include a passage 67 that extends from a distal end of the nozzle 66 to an internal chamber or bay 68 of the insertion cartridge 56. The passage 67 may include a folding chamber 69 that includes a diameter that that tapers inward, as shown. The tapering may facilitate bending or folding of the IOL 10 during delivery of the IOL 10 through the nozzle 66 and into the eye.

Figure 7B:
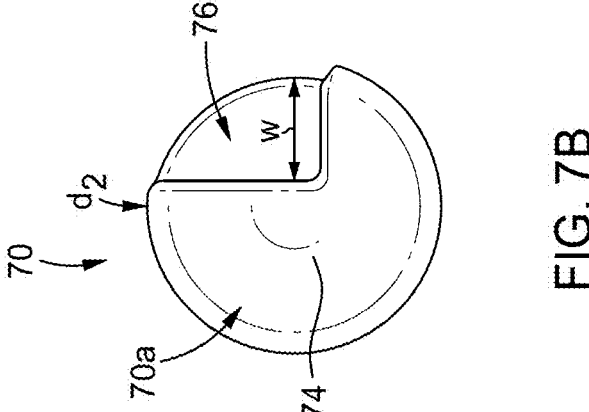
FIG. 7B illustrates a front perspective view of a soft tip in accordance with some embodiments of the present disclosure.
Figure 7A:
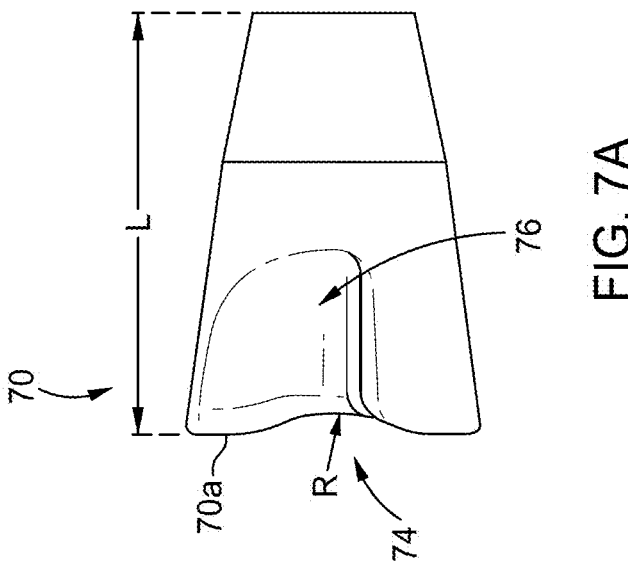
FIG. 7A illustrates a side perspective view of a soft tip in accordance with some embodiments of the present disclosure.

FIG. 7A illustrates a side perspective view of the soft tip 70 in accordance with particular embodiments of the present disclosure. An overall length L of the soft tip 70 may range from about 2 mm to about 6 mm. As shown, a distal end 70a (and surface thereof) includes a dimple or dimple 74 that may have a radius R of curvature ranging from about 0.4 mm to about 0.8 mm (e.g., about 0.65 mm).

Figure 10B:
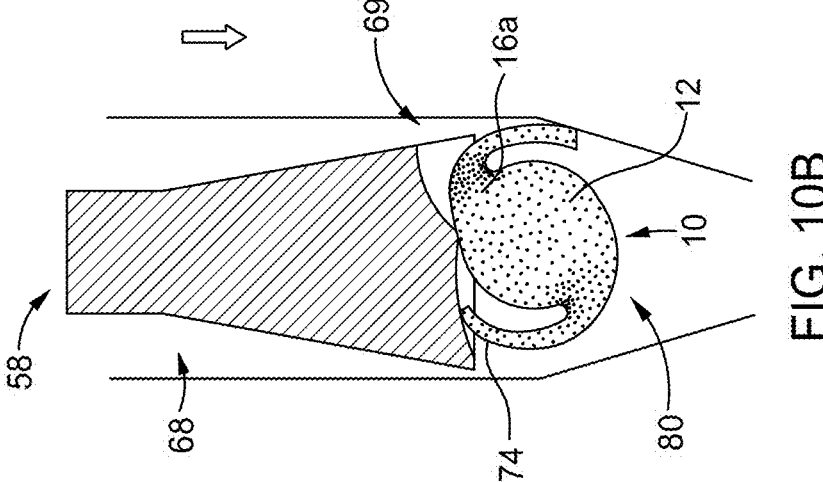
FIG. 10B illustrates a plunger driving an IOL through a folding chamber in accordance with some embodiments of the present disclosure.

In certain embodiments, the dimple 74 may receive a gusset of a trailing haptic extension (e.g., gusset 16a as shown on FIG. 10B) and may guide the gusset into a pocket 76 that may be adjacent to or in fluid communication with the dimple 74, as the IOL 10 is compressed during delivery (e.g., as shown on FIG. 10B). The pocket 76 may include a depth d ranging from about 1 mm to about 4 mm (e.g., about 2.5 mm). In some embodiments, the pocket 76 may occupy about 20% to about 30% (e.g., about 25%) of the distal end 70a, as shown.

FIG. 7B is a front perspective view of the soft tip 70 in accordance with particular embodiments of the present disclosure. The dimple 74 may be positioned at a center of the distal end 70a. The distal end 70a may have a diameter (indicated by the dashed line $d_2$) of about 2 mm or less, for example, ranging from about 1 mm to about 2 mm (e.g., about 1.6 mm) to allow for insertion into incisions smaller than 2 mm. The height h and the width w of the pocket 76 may range from about 0.5 mm to about 1.5 mm (e.g., about 1.3 mm).

FIG. 7C illustrates a lengthwise cross-section of the soft tip of FIG. 7A in accordance with some embodiments of the present disclosure. In particular embodiments, the soft tip 70 may include a passage 71 that extends from an opening 71a positioned at a rear of the soft tip 70, as shown. The passage 71 may have an internal diameter of about 2 mm or less, for example, ranging from about 0.5 mm to less than about 2 mm. The distal end 72 (e.g., shown on FIG. 6) of the plunger 58 may be secured within the passage 71 via a press-fit, for example.

Figure 7D:
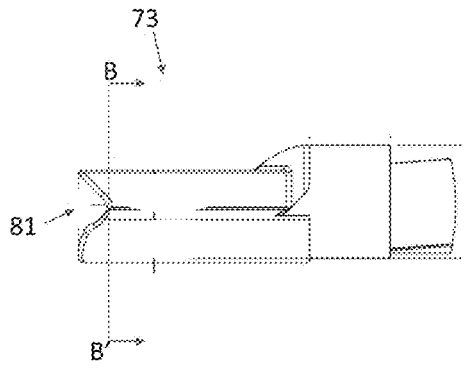
FIG. 7D illustrates a side view of a distal end of the plunger of FIG. 5B in accordance with some embodiments of the present disclosure.

FIG. 7D illustrates a side view of the distal end 73 of FIG. 5B in accordance with some embodiments of the present disclosure. As shown, the distal end 73 includes a recess 81 for attachment to a soft tip (e.g., a soft tip 86 shown on FIG. 7F).

Figure 7E:
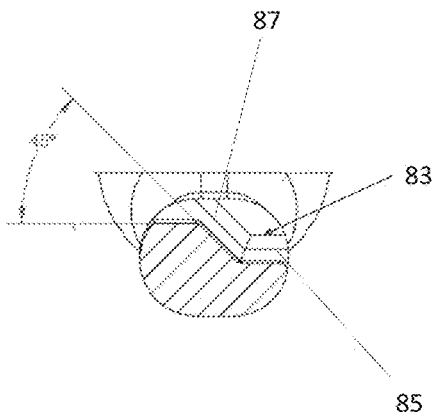
FIG. 7E illustrates a cross-section of a front view of the distal end of FIG. 7D in accordance with some embodiments of the present disclosure.

FIG. 7E illustrates a cross-section of the distal end 73 in accordance with particular embodiments of the present disclosure. The cross-section is taken along the dashed line extending from B to B', as shown on FIG. 7D. As shown, the distal end 73 includes a groove 83. The groove 83 may include a first portion 85 and a second portion 87 that extends at an angle from the first portion 85. For example, the second portion 87 may extend from the first portion 85 at an angle ranging from about 30° to about 60° (e.g., 45°).

Figure 7F:
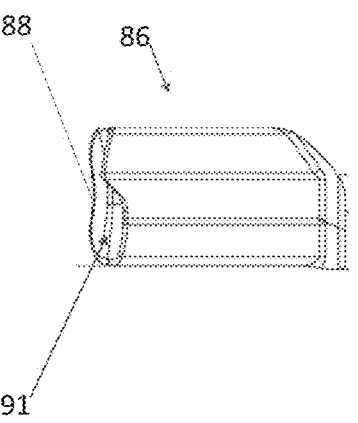
FIG. 7F illustrates a side view of a soft tip in accordance with some embodiments of the present disclosure.

FIG. 7F illustrates a side view of a soft tip 86 that may be overmolded onto the distal end 73 of the plunger 59 in accordance with particular embodiments of the present disclosure. The soft tip 86 may be similar to the soft tip 70.

For example, the soft tip 86 may include a dimple 88 in fluid communication with a pocket 91. The soft tip 86 may include a thickness (e.g., overmold thickness of silicone or TPU) that is at least 0.1 mm. The soft tip 86 may include dimensions similar to the soft tip 70.

Figure 8:
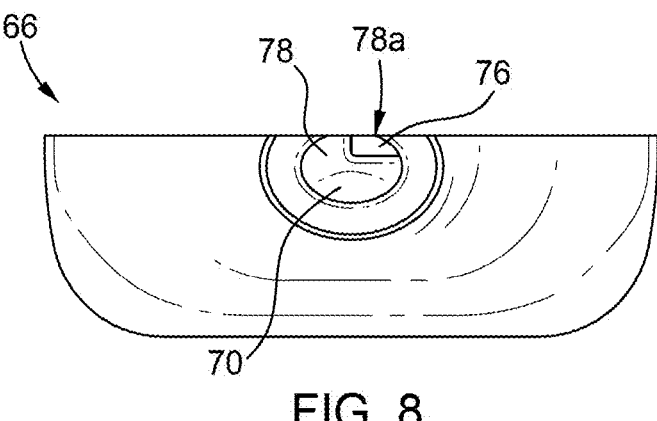
FIG. 8 illustrates a front perspective view of the nozzle in accordance with some embodiments of the present disclosure.

FIG. 8 is a front perspective view of the nozzle 66 in accordance with particular embodiments of the present disclosure. As illustrated, soft tip 70 may be visible in an opening 78 of the nozzle 66. The pocket 76 of the soft tip 70 may be aligned with an upper right quadrant 78*a* of an opening 78 of the nozzle 66, as shown. A diameter of the opening 78 may be about 2 mm or less, for example, range from about 1 mm to about 2 mm.

Figure 9A:
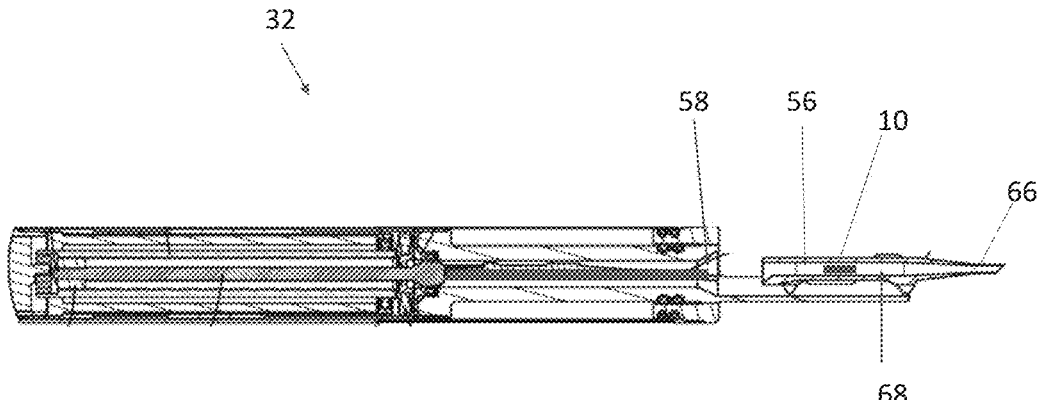
FIG. 9A illustrates a plunger in a retracted position in accordance with some embodiments of the present disclosure.
Figure 9B:
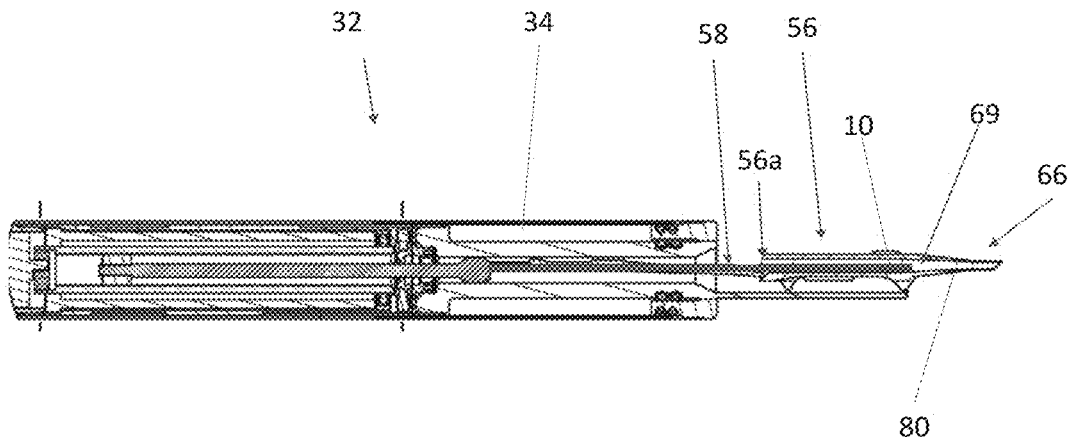
FIG. 9B illustrates a plunger in an extended position in accordance with some embodiments of the present disclosure.

FIGS. 9A and 9B are cross-sections of the insertion tool 32 in accordance with particular embodiments of the present disclosure. The cross-section illustrates a side view taken along the dashed line L$_2$, as shown on FIG. 2A, for example.

FIG. 9A illustrates the insertion tool 32 with the plunger 58 in accordance with particular embodiments of the present disclosure. As shown, the plunger 58 is retracted and positioned within the insertion tool 32. In this initial position, the IOL 10 may be positioned in the bay 68 of the insertion cartridge 56, prior to the advancement stage. The IOL 10 may include the IOL 10 or a component thereof.

FIG. 9B illustrates the insertion tool 32, in the advancement stage, in accordance with particular embodiments of the present disclosure. As shown, the plunger 58 may extend from the housing 34 and may enter the bay 68 via may advance the IOL 10 through the folding chamber 69 to a dwell position in a deployment channel 80 of the nozzle 66. The IOL 10 may be folded (compressed) in the folding chamber 69 as the IOL 10 passes through the folding chamber 69. The IOL 10 may be rolled or folded to reduce a size of the IOL 10. This reduction in size allows delivery of the IOL 10 through a minimally sized (e.g., smaller than 2.0 mm) incision in the eye.

Figure 10A:
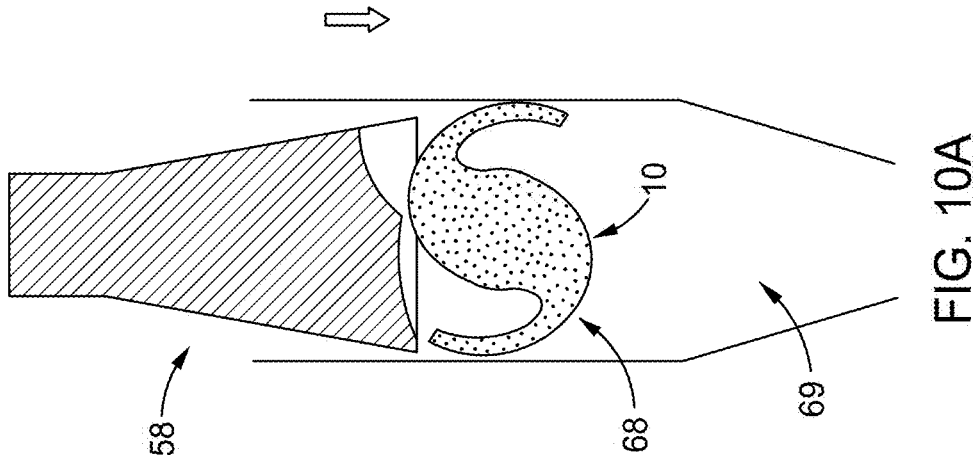
FIG. 10A illustrates a plunger encountering an IOL in accordance with some embodiments of the present disclosure.

FIGS. 10A and 10B are cross-sections of a top view of the insertion cartridge 56 in accordance with particular embodiments of the present disclosure.

FIG. 10A illustrates the plunger 58 encountering the IOL 10 that is disposed within the bay 68. The plunger 58 moves in the direction indicated by the arrow. The plunger 58 may move through the bay 68 via aperture 56*a* of the insertion cartridge 56, as shown. The plunger 58 contacts and moves the IOL 10 through the folding chamber 69 for delivery. The aperture 56*a* may be aligned with the plunger 58.

FIG. 10B illustrates the plunger 58 driving the IOL 10 from the bay 68 through the folding chamber 69 to the deployment channel 80, as shown. The dimple 74 may contact the lens portion 12 and/or a trailing gusset 16*a* of the IOL 10. The pocket 76 receives the trailing gusset 16*a*, thereby providing relief to the trailing gusset 16*a*. This relief may reduce flexion of the trailing gusset 16*a*, thereby preventing damage to the IOL 10. The radius of curvature R (shown on FIG. 7A) may allow the distal end 70*a* to grasp the IOL 10 and allow the IOL 10 to rotate and compress to position the trailing gusset 16*a* in the pocket 76, as shown.

In the deployment stage, the insertion tool 32 may advance the IOL 10 from the dwell position and out the nozzle 66 via the deployment channel 80 and into a patient's eye.

An exemplary technique for implantation of the IOL 10 into an eye 90 of a patient will now be described with respect to FIGS. 11A and 11B.

Figure 11A:
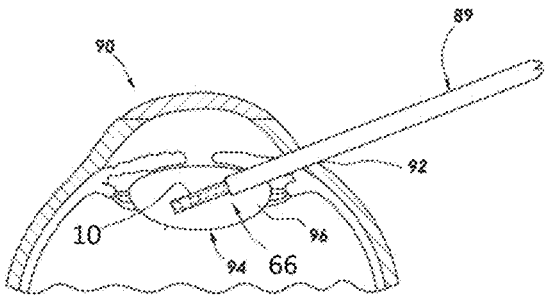
FIGS. 11A and 11B illustrate implantation of an IOL in accordance with some embodiments of the present disclosure.
Figure 11B:
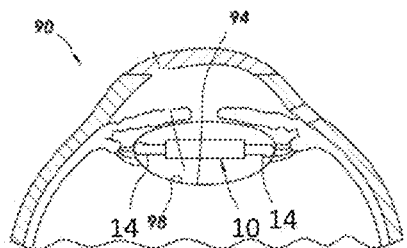

As illustrated on FIG. 11A, an insertion tool 89 that may be similar to the insertion tool 32 (e.g., shown on FIG. 2A) in accordance with particular embodiments of the present disclosure. An incision 92 may be made in the eye 90 by a surgeon. For example, the incision 92 may be made through the sclera 94 of the eye 90. The incision 92 may be a suitable width or length. Without limitation, the suitable width and/or length may be less than 2 millimeters. After the incision 92 is made, the nozzle 66 of the insertion tool 89 may be inserted through the incision 92 into an interior portion 96 of the eye 90. The insertion tool 89 may be actuated to dispense the IOL 10 into a capsular bag 98 of the eye 90.

The IOL 10 may be delivered in a folded (or rolled configuration) and allowed to unfurl after ejection from the insertion tool 32. Upon dispensation, the IOL 10 should unfurl and settle within the capsular bag 98 of the eye 90, as shown on FIG. 11B. The haptic extensions 14 may be manipulated, for example, to engage the inside an equator of the capsular bag 98. The haptic extensions 14 may engage the capsular bag 98 to secure the IOL 10 in the capsular bag 98.

Use of the methods and systems described herein may provide numerous benefits and advantages over other IOL delivery systems. For example, as described herein, the soft tip 70 includes geometry that prevents or mitigates damage to the IOL 10 as it is being compressed during delivery into an eye.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for delivery of an intraocular lens (IOL) into an eye, comprising:

a plunger; and a plunger tip, the plunger tip comprising:

a dimple positioned at a distal end of the plunger tip, wherein a location on the dimple that is closest to a proximal end of the plunger tip is positioned at a center of the distal end, the dimple comprising a continuous curvature extending from a first side of an outer perimeter of the distal end of the plunger tip, through the location at the center of the distal end, to a second, opposing side of the outer perimeter of the plunger tip; and an asymmetrical pocket positioned at the distal end of the plunger tip and defining a portion of the outer perimeter of the distal end of the plunger tip, the asymmetrical pocket comprising (i) a planar sidewall extending from a distal end of the asymmetrical pocket to a proximal end of the asymmetrical pocket and (ii) an arcuate sidewall extending from the distal end of the asymmetrical pocket to the proximal end of the asymmetrical pocket, wherein the asymmetrical pocket is in fluid communication with the dimple, and a portion of the asymmetrical pocket is closer to the proximal end of the plunger tip than the dimple is to the proximal end of the plunger tip, wherein the dimple has a radius of curvature of about 0.4 millimeters to about 0.8 millimeters, the asymmetrical pocket has a depth of about 1.0 millimeters to about 2.5 millimeters, and the distal end of the plunger tip has a diameter of about 2 millimeters or less to allow for insertion into incisions smaller than 2 millimeters, wherein the outer perimeter of the distal end of the plunger tip is generally circular with only a single portion missing from the generally circular outer perimeter, the single portion being about 20% to 30% of a surface area of the generally circular outer perimeter.

2. The apparatus of claim 1, wherein the plunger tip comprises at least one material selected from the group consisting of a styrenic block copolymer, a polyolefin blend, an elastomeric alloy, a thermoplastic polyurethane, a thermoplastic copolyester, a thermoplastic polyamide, and combinations thereof.

3. The apparatus of claim 1, wherein the plunger comprises at least one material selected from the group consisting of polystyrene, acrylonitrile butadiene styrene, polycarbonate, polyamide, polyimide, polyetherimide, polyarylamide, polyetheretherketone, polybutylene terephthalate, polypropylene, polysulphone, liquid crystal polymer, and combinations thereof.

4. The apparatus of claim 1, wherein a width of the asymmetrical pocket ranges from 0.5 millimeters to 1.5 millimeters.

5. The apparatus of claim 1, wherein the plunger tip is an overmold on the plunger, wherein the plunger tip comprises silicone, wherein the plunger comprises polycarbonate and a thickness of the overmold is at least 0.1 mm.

6. The apparatus of claim 1, wherein the plunger tip is made of a material with a Shore A durometer value ranging from 30 to 95.

7. An apparatus for delivery of an intraocular lens (IOL) into an eye, comprising:
  a nozzle;
  a cartridge, the cartridge coupled to the nozzle;
  a plunger aligned with an aperture of the cartridge; and
  a plunger tip, the plunger tip comprising:
    a dimple positioned at a distal end of the plunger tip, wherein a location on the dimple that is closest to a proximal end of the plunger tip is positioned at a center of the distal end, the dimple comprising a continuous curvature extending from a first side of an outer perimeter of the distal end of the plunger tip, through the location at the center of the distal end, to a second, opposing side of the outer perimeter of the plunger tip; and
    an asymmetrical pocket positioned at the distal end of the plunger tip and defining a portion of the outer perimeter of the distal end of the plunger tip, the asymmetrical pocket comprising (i) a planar sidewall extending from a distal end of the asymmetrical pocket to a proximal end of the asymmetrical pocket and (ii) an arcuate sidewall extending from the distal end of the asymmetrical pocket to the proximal end of the asymmetrical pocket, wherein the asymmetrical pocket is in fluid communication with the dimple, and a portion of the asymmetrical pocket is closer to the proximal end of the plunger tip than the dimple is to the proximal end of the plunger tip, wherein the dimple has a radius of curvature of about 0.4 millimeters to about 0.8 millimeters, the asymmetrical pocket has a depth of about 1.0 millimeters to about 2.5 millimeters, and the distal end of the plunger tip has a diameter of about 2 millimeters or less to allow for insertion into incisions smaller than 2 millimeters,
  wherein the outer perimeter of the distal end of the plunger tip is generally circular with only a single portion missing from the generally circular outer perimeter, the single portion being about 20% to 30% of a surface area of the generally circular outer perimeter.

8. The apparatus of claim 7, wherein the cartridge comprises the IOL.

9. The apparatus of claim 8, wherein the IOL comprises haptics.

10. The apparatus of claim 7, wherein the plunger tip comprises silicone, and the plunger comprises polycarbonate.

11. A method for delivery of an intraocular lens (IOL) into an eye, comprising:
  inserting a nozzle of an insertion tool into the eye through an incision, wherein the insertion tool further comprises:
    a plunger; and
    a plunger tip, the plunger tip comprising:
      a dimple positioned at a distal end of the plunger tip, wherein a location on the dimple that is closest to a proximal end of the plunger tip is positioned at a center of the distal end, the dimple comprising a continuous curvature extending from a first side of an outer perimeter of the distal end of the plunger tip, through the location at the center of the distal end, to a second, opposing side of the outer perimeter of the plunger tip; and
      an asymmetrical pocket positioned at the distal end of the plunger tip and defining a portion of the outer perimeter of the distal end of the plunger tip, the asymmetrical pocket comprising (i) a planar sidewall extending from a distal end of the asymmetrical pocket to a proximal end of the asymmetrical pocket and (ii) an arcuate sidewall extending from the distal end of the asymmetrical pocket to the proximal end of the asymmetrical pocket, wherein the asymmetrical pocket is in fluid communication with the dimple, and a portion of the asymmetrical pocket is closer to the proximal end of the plunger tip than the dimple is to the proximal end of the plunger tip, wherein the dimple has a radius of curvature of about 0.4 millimeters to about 0.8 millimeters, the asymmetrical pocket has a depth of about 1.0 millimeters to about 2.5 millimeters, and the distal end of the plunger tip has a diameter of about 2 millimeters or less to allow for insertion into incisions smaller than 2 millimeters,
  wherein the outer perimeter of the distal end of the plunger tip is generally circular with only a single portion missing from the generally circular outer perimeter, the single portion being about 20% to 30% of a surface area of the generally circular outer perimeter shape.

\* \* \* \* \*